United States Patent [19]

Kirchlechner et al.

[11] Patent Number: 5,075,452
[45] Date of Patent: Dec. 24, 1991

[54] PROCESS FOR THE PREPARATION OF 5-MEMBERED NITROGEN CONTAINING HETEROAROMATICS

[75] Inventors: Richard Kirchlechner, Rott; Michael Casutt, Erzhausen; Arno Basedow, Bad Vilbel, all of Fed. Rep. of Germany

[73] Assignee: Merck Patent Gesellschaft Mit Beschränkter Haftung, Darmstadt, Fed. Rep. of Germany

[21] Appl. No.: 445,603

[22] PCT Filed: Mar. 25, 1989

[86] PCT No.: PCT/EP89/00335
§ 371 Date: Dec. 6, 1989
§ 102(e) Date: Dec. 6, 1989

[87] PCT Pub. No.: WO89/09768
PCT Pub. Date: Oct. 19, 1989

[30] Foreign Application Priority Data

Apr. 7, 1988 [DE] Fed. Rep. of Germany ....... 3811621

[51] Int. Cl.$^5$ ............... C07D 233/90; C07D 207/34; C07D 405/06

[52] U.S. Cl. ................... 548/343; 548/528; 548/531; 548/536; 548/537; 548/561; 544/129; 544/130; 544/139; 544/141; 546/187; 546/208; 546/210

[58] Field of Search ............... 548/343, 536, 531, 528, 548/537, 561; 544/139, 141, 129, 130; 546/187, 208, 210

[56] References Cited

FOREIGN PATENT DOCUMENTS 0207563 1/1987 European Pat. Off. .
0306868 3/1989 European Pat. Off. .
1184709 7/1959 France .

*Primary Examiner*—Mary C. Lee
*Assistant Examiner*—Lenora Miltenberger
*Attorney, Agent, or Firm*—Millen, White & Zelano

[57] ABSTRACT

Compounds of the formula I

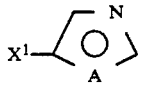

in which A and $X^1$ have the meaning given in patent claim 1 can be prepared in a simple manner, in a one-pot process and in high yields.

5 Claims, No Drawings

PROCESS FOR THE PREPARATION OF 5-MEMBERED NITROGEN CONTAINING HETEROAROMATICS

The invention relates to a process for the preparation of compounds of the formula I

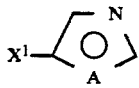

in which
A is $NR^1$ or $CH-X^2$,
$X^1$ and $X^2$ are each independently of one another $CO-OR^2$, $CO-NR^3R^4$ or CN,
$R^1$ and $R^2$ are each independently of one another hydrogen, alkyl having 1-8 C atoms or a carbocyclic radical and
$R^3$ and $R^4$ are each independently of one another alkyl having 1-7 C atoms, aryl having 6-8 C atoms or aralkyl having 7-13 C atoms or are each together with the adjacent nitrogen atom also a heterocyclic radical having 2-6 C atoms, in which a $CH_2$ group can also be replaced by O, S or NH.

The object of the invention was to provide a novel process for the preparation of compounds of the formula I which makes these compounds available by means of simple reactions in a high yield.

Compounds of the formula I are useful synthetic intermediates; the compounds of the formula Ia

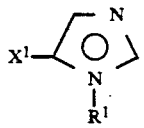

in which $R^1$ and $X^1$ have the meaning mentioned are used in particular in the synthesis of imidazole alkaloids such as, for example, isomacrorine or pilocarpine.

Ia ($X^1=COOR^2$) can be prepared according to EP-OS 0,207,563 in 4 steps starting from N-alkylglycine ester hydrochlorides.

Starting from diethyl N-methylacetaminomalonate, Ia ($R^1=CH_3$, $X^1=COOR^2$) is obtained in a 5-step synthesis.

In another 5-step synthesis, diaminomaleonitrile can be reacted with triethyl orthoformate to give the imidazole-4,5-dinitrile which, after alkylation with dimethyl sulfate, hydrolysis and partial decarboxylation by heating in acetic anhydride, gives the compound of the formula Ia ($R^1=CH_3$, $X^1=COOH$).

However, all these processes are characterized by a large number of synthetic steps and accordingly a low total yield.

Although it is known that 1,3,4-triazoles are obtained by reaction of 3-dimethylamino-2-azaprop-2-en-1-ylidene-dimethylammonium chloride (Gold's reagent) with hydrazines, no mention is made of the fact that this reagent can also be used for the preparation of other 5-membered heterocycles.

Surprisingly, it has now been found that compounds of the formula I, in particular of the formula Ia, can be prepared by reaction of methylene compounds of the formula II or acid addition salts thereof with aminomethyleneformamidinium salts of the formula III in a single synthetic step, in a one-pot process and in high yields.

The invention accordingly relates to a process for the preparation of compounds of the formula I

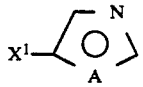

in which
A is $NR^1$ or $CH-X^2$,
$X^1$ and $X^2$ are each independently of one another $CO-OR^2$, $CO-NR^3R^4$ or CN,
$R^1$ and $R^2$ are each independently of one another hydrogen, alkyl having 1-7 C atoms or a carbocyclic radical and
$R^3$ and $R^4$ are each independently of one another alkyl having 1-8 C atoms, aryl having 6-8 C atoms or aralkyl having 7-13 C atoms or are each together with the adjacent nitrogen atom also a heterocyclic radical having 2-6 C atoms, in which a $CH_2$ group can also be replaced by O, S or NH,
which is characterized in that a methylene compound of the formula II

$$X'-CH_2-AH \qquad II$$

or one of its acid addition salts in which $X^1$ and A have the meaning mentioned is reacted with a salt of the formula III

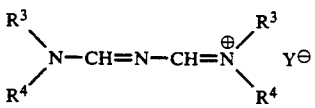

in which
$R^3$ and $R^4$ have the meaning mentioned and
$Y^\ominus$ is $Cl^\ominus$, $Br^\ominus$, $I_3^\ominus$, $ClO_4^\ominus$ or $BF_4^\ominus$,
and a base.

The invention in particular relates to a process for the preparation of compounds of the formula Ia in which A is $NR^1$, and the compound of the formula IIa is reacted in the form of an acid addition salt with a compound of the formula III.

The invention also relates to the use of the compounds of the formula I, in particular of the formula Ia, prepared by the process according to the invention for the preparation of active compounds in medicaments, in particular pilocarpine.

The process according to the invention gives, regardless of the nature of groups A, $X^1$, $X^2$, $R^1$, $R^2$, $R^3$, $R^4$ and $X^\ominus$, the corresponding compounds of the formula I without exception in high yields.

If A is $NR^1$ and $X^1$ is $COOR^2$, $R^1$ and $R^2$ are each independently of one another hydrogen, alkyl having 1-7 C atoms or are carbocyclic radicals.

If $R^1$ and/or $R^2$ are an alkyl radical, this radical can be straight-chain or branched. Accordingly, it is methyl, ethyl, n-propyl, n-butyl, n-pentyl, n-hexyl, n-heptyl, n-octyl, i-propyl, 1-(or 2)methyl-propyl, tert.-butyl, 1-(2- or 3-)methylbutyl, neo-pentyl, 1-(2-, 3- or 4-)methylpentyl or 1-(2-, 3-, 4- or 5-)methylhexyl or 2-ethylhexyl (i-octyl). Preferably, it is methyl, ethyl or i-propyl, in particular methyl.

If $R^1$ and/or $R^2$ are a carbocyclic radical, this radical can be aromatic, cycloaliphatic or araliphatic. Accordingly, it is preferably phenyl, benzyl, cyclohexyl, 1-indanyl, tetrahydronaphthyl (for example 1,2,3,4-tetrahydro-1-naphthyl), benzocycloheptyl, (for example 5-benzocycloheptyl), 9,10-dihydro-9-anthracenyl, 9H-fluor-en-9-yl, 5-dibenzo[a,d]cycloheptyl or dihydronaphthyl (for example 1,2-dihydro-1-naphthyl).

Each of the abovementioned carbocyclic radicals can be unsubstituted or substituted by 1 to 6 substituents selected from the group consisting of alkyl, alkoxy having 1-5 C atoms and halogen.

The $R^3R^4N$ group is preferably a N,N-dimethyl-, N,N-diethyl-, N,N-dipropyl-, N,N-diisopropyl-, N,N-dibutyl-, N,N-diisobutyl-, N,N-di-sec-butyl-, N,N-dicyclohexyl-, N,N-dibenzyl-, N,N-diphenyl- or N,N-di-(o-, m- or p-tolyl)-amino radical or is a morpholino, piperidino or N-methylanilino radical.

Neither is the meaning of the anion $Y^\ominus$ critical for the course of the reaction; preferably it is $Cl^\ominus$ or $Br^\ominus$.

The starting materials of the formula II are known (IIa: $A = NR^1$: glycine or aminoacetonitrile derivatives; IIb: $A = CH-X^2$: succinic acid derivatives) or can be prepared by known methods, such as those described in the literature (for example in standard works such as Houben-Weyl, Methoden der Organischen Chemie (Methods of Organic Chemistry), Georg Thieme Verlag, Stuttgart) under reaction conditions, such as are known and suitable for the reactions mentioned. It is also possible to use variations of these methods which are known per se and not mentioned here in detail.

The starting materials of the formula III are also known and can be prepared from cyanuric chloride and N,N-dialkylformamides.

The reaction of the methylene compound of the formula II with the salt of the formula III is preferably carried out in an inert solvent in the presence of a base. Suitable bases, dependent on C—H acidity of the methylene compound used, are, for example, alkali metal or alkaline earth metal hydroxides such as lithium hydroxide, calcium hydroxide, barium hydroxide, sodium hydroxide or potassium hydroxide, alkali metal carbonates such as sodium carbonate or potassium carbonate, alcoholates such as sodium methylate, sodium ethylate, lithium ethylate or potassium tert.-butylate, alkali metal amides such as potassium amide or sodium amide, or organic bases such as triethylamine, pyridine, 4-N,N-dimethylaminopyridine, lutidine, piperidine, morpholine, piperazine, collidine or quinoline, lithium diisopropylamide or lithium tetramethylpiperidide.

The reaction is preferably carried out in an inert solvent. Suitable inert solvents are preferably ethers such as diethyl ether, ethylene glycol dimethyl ether, tetrahydrofuran, tert.-butyl methyl ether or dioxane, and also amides such as dimethylformamide, N,N-dimethylpropyleneurea, dimethylacetamide or N-methylpyrrolidone, furthermore sulfoxides such as dimethyl sulfoxide or sulfones such as sulfolane and hydrocarbons such as pentane, hexane, cyclohexane, benzene or toluene. The reaction temperatures are preferably, depending on the reactivity of the methylene compound used, between $-78°$ C. and $+150°$ C., preferably between $+20°$ C. and $+100°$ C., and the reaction times between 1 and 48 hours.

In the reaction of the compounds of the formula II in which $X^1$ is $CO-OR^2$ with the salt of the formula III, not only the carboxylic esters of the formula I in which $X^1$ is $CO-OR^2$ but also the carboxamides of the formula I in which X is $CO-NR^3R^4$ can be formed as a result of the reactivity of these educts. The ratio of the products formed can be easily controlled by suitable selection of the reaction conditions.

For complete separation of the formation of carboxamides of the formula I, it is advantageous to carry out the reaction in the presence of non-enolizable carboxylic esters which are suitable for trapping the amines which are formed during the reaction from the salt of the formula III. Particularly suitable non-enolizable carboxylic esters are the methyl or ethyl esters of the corresponding carboxylic acid such as, for example, benzoic acid, phthalic acid or terephthalic acid, perfluoroalkanecarboxylic acids such as, for example, trifluoroacetic acid, or of the aliphatic carboxylic acid which does not have hydrogen atoms in the α-position relative to the carboxyl group, such as, for example, pivalic acid or oxalic acid.

On the other hand, the carboxamides of the formula I in which $X^1$ or $X^2$ and $X^2$ are $CO-NR^3R^4$ can also be prepared selectively by carrying out the reaction without the addition of these carboxylic esters a elevated temperature and longer reaction times.

Preferably, compounds of the formula IIa (A is $NR^1$) are used in the form of their acid addition salts IIa'

$$X^1-CH_2-NHR^1 \cdot HY^1 \qquad IIa'$$

Examples of $Y^1$ are inorganic acid radicals such as F, Cl, Br, I, $I_3$, $HSO_4$, $H_2PO_4$ or $ClO_4$, but also organic acid radicals such as carboxylates, in particular acetate or trifluoroacetate, or sulfonates, in particular p-toluenesulfonate, trifluoromethanesulfonate or methanesulfonate. The chlorides are particularly preferred.

In a particularly preferred embodiment of the process according to the invention, a hydrochloride of the formula IIa ($Y^1 = Cl$) is added together with an aminomethyleneformamidinium chloride ($Y = Cl$) of the formula III at $-10°$ C. to $+30°$ C. to a mixture of an alkali metal alcoholate, preferably sodium methylate or sodium ethylate, and an inert solvent, preferably a hydrocarbon such as cyclohexane or toluene, or an ether such as, for example, dioxane or tetrahydrofuran, and the mixture is subsequently stirred at temperatures between 0° and 130° C for 1 to 30 hours.

Compounds of the formula I, in particular of the formula Ia, are known and can be reacted by known methods, such as described, for example, in Helv. Chim. Acta 55, 1053-1062 (1972) or J. Org. Chem 51, 1713-1719 (1986) to give pilocarpine.

The 5-membered nitrogen-containing heterocycles which can be prepared by the process according to the invention are furthermore useful starting materials for the preparation of dyes, plant protection agents and other pharmaceutical or are themselves suitable, as disclosed, for example, in EP-OS 0,207,563, as agents for influencing plant growth.

The process according to the invention thus makes it possible to prepare the compounds of the formula I, in particular of the formula Ia, in a simple manner in high yields from easily accessible inexpensive starting materials in a single synthetic step to be carried out in a one-pot process and thus represents a significant advance in the area of the synthesis of compounds of the formula I, in particular in the synthesis of pilocarpine.

The examples which follow are intended to illustrate the invention without limiting it:

EXAMPLE 1

17.45 g of sarcosine methyl ester hydrochloride and 31.09 g of 3-dimethylamino-2-azaprop-2-en-1-ylidene dimethylammonium chloride are added in succession at room temperature to a suspension of 16.21 g of sodium methylate in 300 ml of toluene kept under nitrogen, and the mixture is stirred at 70° C. for 24 hours. It is then decanted, the residue is extracted three times with toluene, and the combined extracts concentrated.

The residue is chromatographed on silica gel (ethyl acetate) to give 15.1 g of methyl 1-methyl-1H-imidazole-5-carboxylate; b.p.: 115° C./8 torr, sublimation at 25° C./0.01 torr, m.p. 56° C..

Analogously, dimethyl succinate gives dimethyl pyrrole-3,4-dicarboxylate;

N-(9-fluorenyl)-glycine methyl ester hydrochloride gives methyl 1-(9-fluorenyl)-1H-imidazole-5-carboxylate;

N-(1,2,3,4-tetrahydronaphthalene-1-yl)-glycine methyl ester hydrochloride gives methyl 1-(1,2,3,4-tetrahydronaphthalene-1-yl)-1-H-imidazole-5-carboxylate, m.p. 63° C.; N-methylaminoacetonitrile gives 1-methyl-1H-imidazole-5-carbonitrile;

N-benzyl-glycine benzyl ester hydrochloride gives benzyl 1-benzyl-1H-imidazole-5-carboxylate;

sodium ethylate/sarcosine ethyl ester hydrochloride gives ethyl 1-methyl-1H-imidazole-5-carboxylate;

N-(9-fluorenyl)-glycine benzyl ester hydrochloride gives benzyl 1-(9-fluorenyl)-1H-imidazole-5-carboxylate.

Using glycine ester hydrochlorides, the following compounds are obtained analogously:
methyl 1-H-imidazole-5-carboxylate
ethyl 1-H-imidazole-5-carboxylate, m.p. 158° C.
benzyl 1-H-imidazole-5-carboxylate Using N-substituted glycine ester hydrochlorides, the following compounds are obtained analogously: methyl 1-isopropyl-1-H-imidazole-5-carboxylate, b.p. 130° C./13 torr methyl 1-cyclohexyl-1-H-imidazole-5-carboxylate, m.p. 90° C.

methyl 1-benzyl-1-H-imidazole-5-carboxylate, m.p. 64° C.

ethyl 1-phenyl-1-H-imidazole-5-carboxylate, m.p. 81° C.

methyl 1-(2ethylhexyl)-1H-imidazole-5-carbonylate

EXAMPLE 2

A suspension of 189.07 g of sodium methylate in 2,000 ml of dioxane is initially introduced under nitrogen at room temperature, 181.45 g of sarcosine methyl ester hydrochloride and 261.84 g of 3-dimethylamino-2 -azaprop-2-en-1-ylidene dimethylammonium chloride are then added in succession with stirring, and the reaction mixture is stirred at 60° C. for 24 hours.

The mixture is then filtered off with suction, the solid is washed with dioxane, and the filtrate is concentrated.

The residue is chromatographed on silica gel (ethyl acetate) to give 152.1 g of methyl 1-methyl-1H-imidazole-5-carboxylate, m.p. 55° C. to 56° C.. $^1$H-NMR (200 MHz, CDCl$_3$): $\delta = 7.72$ (br s, 1H); 7.55 (br s, 1H); 3.90 (s, 3H); 3.84 (s, 3H).

EXAMPLE 3

A suspension of 54.03 g of sodium methylate in 600 ml of dioxane is initially introduced at room temperature under nitrogen, 41.87 g of sarcosine methyl ester hydrochloride, 65.46 g of 3-dimethylamino-2-azaprop-2-en-1-ylidene dimethylammonium chloride and 47.24 g of dimethyl oxalate are added in succesion, and the reaction mixture is stirred at 65° C. for 12 hours. The mixture is then filtered off with suction through kieselguhr, the solid is washed with dioxane, and the filtrate is concentrated under reduced pressure.

The residue is chromatographed on silica gel (ethyl acetate) to give 33.2 g of methyl 1-methyl-1H-imidazole-5-carboxylate of melting point 55° C.

EXAMPLE 4

13.96 g of sarcosine methyl ester hydrochloride and 21.27 g of 3-dimethylamino-2-azaprop-2-en-1-ylidene dimethylammonium chloride are added in succession at room temperature to a suspension of 16.21 g of sodium methylate in 200 ml of tetrahydrofuran kept under nitrogen, and the mixture is stirred at the reflux temperature for 6 hours.

The mixture is then cooled to room temperature, filtered through kieselguhr, the solid is washed with tetrahydrofuran, and the filtrate is concentrated under reduced pressure.

The residue is chromatographed on silica gel (ethyl acetate) to give 11.3 g of methyl 1-methyl-1 H-imidazole-5-carboxylate; m.p. 55°–56° C.

EXAMPLE 5

A suspension of 162 g of sodium methylate in 2,000 ml of dioxane is initially introduced at room temperature under nitrogen, 139.6 g of sarcosine methyl ester hydrochloride and 212.7 g of 3-dimethylamino-2-azaprop-2-en-1-ylidene dimethylammonium chloride are added in succession with stirring, and the reaction mixture is stirred at 90° C. for 24 hours.

The mixture is then filtered off with suction, the solid is washed with dioxane, and the filtrate is concentrated under reduced pressure.

Distillation of the residue in vacuo gives 89.3 g of N,N-dimethyl-1-methyl-1H-imidazole-5-carboxamide; m.p. 46°–47° C.

EXAMPLE 6

A mixture of 4.5 g of dibenzyl succinate and 10 of tetrahydrofuran are added at -78° C. to a mixture of lithium diisopropylamide (prepared from 3.0 g of diisopropylamine and 19 ml of a 15% solution of n-butyllithium in hexane) and 15 ml of tetrahydrofuran kept under nitrogen. After warming to 0° C., 3.1 g of 3-dimethylamino-2-azaprop-2-en-1-ylidene dimethylammonium chloride are added, and the mixture is stirred at the boiling temperature for 24 hours. After the addition of 25 ml of a saturated ammonium chloride solution, the aqueous phase is extracted three times with ether, and the combined extracts are concentrated. The residue is chromatographed on silica gel (ethyl acetate) to give benzyl pyrrole-3,4-dicarboxylate.

The following compounds are prepared analogously:
methyl pyrrole-3,4-dicarboxylate
ethyl pyrrole-3,4-dicarboxylate
isopropyl pyrrole-3,4-dicarboxylate
methyl 4-cyanopyrrole-3-carboxylate
3,4-dicyanopyrrole

WORKING EXAMPLE A

Potassium hydride (4.15 g, 35% suspension in oil) is washed twice with 15 ml of hexane and suspended in 150 ml of diethylene glycol..11.6 g of diethyl (cyano(1-

(tert.-butoxycarbonyl)propyl)methyl)phosphonate (prepared according to reference:) are added at 0° C. to this mixture. After stirring at room temperature for 1 hour, a mixture of 4.0 g of 1-methyl-1-H-imidazole-5-carboxaldehyde (prepared from methyl 1-methyl-1-H-imidazolecarboxylate according to references) and 20 ml of diethylene glycol are added, and the mixture is stirred at room temperature for 12 hours. After addition of water and separation of the layers the aqueous layer is extracted 3 times with 200 ml of ether. Concentration of the combined extracts gives an E/Z mixture of tert.-butyl 3-cyano-2-ethyl-4-(1-methyl-1H-5-imidazolyl)-3-butenoate. According to reference[1], this gives in 5 steps (+)-isopilocarpine (m.p. 159° C., $\alpha_D = +34.3°$ (c=1.804, water) after conversion into the nitrate), from which (+)-pilocarpine is obtained by epimerization:

0.97 ml of a 15% solution of n-butyllithium in hexane is added at 0° C. to a solution of 0.21 ml of diisopropylamine in tetrahydrofuran. After stirring for 15 minutes and cooling to −78° C., 100 mg of (+)-isopilocarpine dissolved in 1 ml of tetrahydrofuran are added, and the mixture is stirred at −78° C. for 10 hours. After the addition of 1 g of 2,6-di-tert.-butyl-4-methylphenol, warming to room temperature and addition of 15 ml of hydrochloric acid (0.5 N), the layers are separated. The aqueous layer is washed twice with 25 ml of chloroform. Concentration of the organic layer and preparative separation on an HPLC column gives optically pure (+)-pilocarpine which is converted into the pilocarpine nitrate, m.p. 174° C., $\alpha_D = +81°$ (c=1.618, water) with nitric acid (65%) in ethanol. Reference[1]: R. S. Compagnone, H. Rapoport, J. Org. Chem. 51, 1713-1719 (1986)

Reference[2]: H. Link, K. Bernauer, Helv. Chim. Acta 55, 1053-1062 (1972)

We claim:

1. A process for the preparation of compounds of formula I $$X^1 - \underset{A}{\underset{|}{\diamond}} \overset{N}{\diamond}$$
  I wherein A is $NR^1$ or $CH-X^2$, $X^1$ and $X^2$ are each independently of one another $CO-OR^2$, $CO-NR^3R^4$ or $CN$, $R^1$ and $R^2$ are each independently of one another hydrogen, $C_{1-8}$-alkyl, a carbocylic radical selected from the group consisting of phenyl, benzyl, cyclohexyl, 1-indanyl, tetrahydronaphthyl, benzocycloheptyl, 9,10-dihydro-9-antracenyl, 9H-fluoren-9-yl, 5-dibenzyo[a,d]cycloheptyl and dihydronaphthyl, or such a carbocyclic radical substituted by 1 to 6 halogen atoms, $C_{1-5}$-alkyl- or $C_{1-5}$-alkoxy-, $R^3$ and $R^4$ are each independently $C_{1-8}$-alkyl, $C_{6-8}$-aryl, or $C_{7-13}$-aralkyl or are each together with the adjacent nitrogen atom a heterocyclic radical selected from the group consisting of morpholine and piperidine, said process comprising reacting a base and a methylene compound of the formula II $$X' - CH_2 - AH$$
  II or one of its acid addition salts in which $X^1$ and A have the meaning above with an N,N'-tetrasubsituted aminomethyleneformamidinium salt of the formula III $$\underset{R^4}{\overset{R^3}{\diagdown}} N - CH = N - CH = \overset{\oplus}{\underset{R^4}{\overset{R^3}{\diagup}}} \quad Y^\ominus$$
  III in which $R^3$ and $R^4$ have the meaning above and is $Cl^\ominus$, $Br^\ominus$, $I^\ominus$, $ClO_4^\ominus$ or $BF_4^\ominus$.

2. A process according to claim 1, wherein A is $NR^1$ and the compound of the formula II is reacted in the form of an acid addition salt with a compound of the formula III.

3. A process according to claim 1 wherein the base used is a metal alcoholate.

4. A process according to claim 2 wherein X' is $CO-OR^2$ and the reaction is carried out in the presence of an non-enolizable carboxylic ester.

5. A process according to claim 4, wherein the non-enolizable carboxylic ester is dimethyl oxalate.

* * * * *